(12) United States Patent
Khamene et al.

(10) Patent No.: US 7,724,943 B2
(45) Date of Patent: May 25, 2010

(54) RAPID AND ROBUST 3D/3D REGISTRATION TECHNIQUE

(75) Inventors: Ali Khamene, Princeton, NJ (US); Frank Sauer, Princeton, NJ (US); Chenyang Xu, Allentown, NJ (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 925 days.

(21) Appl. No.: 11/109,119

(22) Filed: Apr. 19, 2005

(65) Prior Publication Data

US 2005/0249398 A1 Nov. 10, 2005

Related U.S. Application Data

(60) Provisional application No. 60/564,145, filed on Apr. 21, 2004.

(51) Int. Cl.
*G06K 9/00* (2006.01)
*G06T 17/00* (2006.01)
*G06T 15/00* (2006.01)

(52) U.S. Cl. ............ 382/154; 382/131; 382/128; 348/E13.057; 348/E13.054; 345/424; 345/419

(58) Field of Classification Search ............ None
See application file for complete search history.

(56) References Cited

U.S. PATENT DOCUMENTS

| | | | | |
|---|---|---|---|---|
| 5,138,698 A * | 8/1992 | Aldrich et al. | ............ | 345/427 |
| 5,182,663 A * | 1/1993 | Jones | ............ | 349/113 |
| 5,297,241 A * | 3/1994 | Hirr et al. | ............ | 345/427 |
| 6,008,814 A * | 12/1999 | Baldwin et al. | ............ | 345/427 |
| 6,081,270 A * | 6/2000 | Berry et al. | ............ | 345/419 |
| 6,181,348 B1 * | 1/2001 | Geiger | ............ | 345/583 |
| 6,322,505 B1 * | 11/2001 | Hossack et al. | ............ | 600/437 |
| 6,385,335 B1 * | 5/2002 | Rudd et al. | ............ | 382/154 |
| 6,393,141 B1 * | 5/2002 | Cronshaw et al. | ............ | 382/141 |
| 6,421,454 B1 * | 7/2002 | Burke et al. | ............ | 382/131 |
| 6,468,218 B1 * | 10/2002 | Chen et al. | ............ | 600/443 |
| 6,501,272 B1 * | 12/2002 | Haacke et al. | ............ | 324/306 |
| 6,553,152 B1 * | 4/2003 | Miller et al. | ............ | 382/294 |
| 6,690,828 B2 * | 2/2004 | Meyers | ............ | 382/218 |
| 6,782,124 B2 * | 8/2004 | Gloersen | ............ | 382/154 |
| 7,120,283 B2 * | 10/2006 | Thieret et al. | ............ | 382/131 |
| 7,150,716 B2 * | 12/2006 | Jones et al. | ............ | 600/446 |
| 7,204,640 B2 * | 4/2007 | Fu et al. | ............ | 378/205 |
| 7,616,198 B2 * | 11/2009 | Herken et al. | ............ | 345/419 |
| 2001/0045955 A1 * | 11/2001 | Oka | ............ | 345/582 |
| 2002/0097906 A1 * | 7/2002 | Ishiyama | ............ | 382/154 |
| 2002/0122577 A1 * | 9/2002 | Allouche | ............ | 382/131 |
| 2003/0026469 A1 * | 2/2003 | Kreang-Arekul et al. | ............ | 382/132 |

(Continued)

OTHER PUBLICATIONS www.Merriam-Webster.com copyright 2009, definition for encode.*

(Continued)

*Primary Examiner*—Vikkram Bali
*Assistant Examiner*—Michelle Entezari

(57) ABSTRACT

Exemplary methods are provided. In one exemplary method, a lower-dimension signature is generated for each of a plurality of data sets of a given dimension. Registration is performed on the lower-dimension signatures. In another exemplary method, a two-dimensional signature is generated for each of a plurality of three-dimensional volumes. Registration is performed on the two-dimensional signatures.

15 Claims, 2 Drawing Sheets

U.S. PATENT DOCUMENTS

| | | | |
|---|---|---|---|
| 2003/0031380 A1* | 2/2003 | Song | 382/284 |
| 2003/0055335 A1* | 3/2003 | Sauer et al. | 600/443 |
| 2003/0097068 A1* | 5/2003 | Hossack et al. | 600/443 |
| 2004/0013290 A1* | 1/2004 | Krishnan et al. | 382/128 |
| 2004/0215071 A1* | 10/2004 | Frank et al. | 600/407 |
| 2005/0018891 A1* | 1/2005 | Barfuss et al. | 382/131 |
| 2005/0041781 A1* | 2/2005 | Jefferson | 378/210 |
| 2005/0043619 A1* | 2/2005 | Sumanaweera et al. | 600/437 |
| 2005/0049477 A1* | 3/2005 | Fu et al. | 600/407 |
| 2005/0065421 A1* | 3/2005 | Burckhardt | 600/407 |
| 2006/0173324 A1* | 8/2006 | Cohen-Bacrie et al. | 600/440 |
| 2007/0189455 A1* | 8/2007 | Allison | 378/95 |
| 2008/0049014 A1* | 2/2008 | Haimerl et al. | 345/419 |

OTHER PUBLICATIONS www.Merriam-Webster.com copywright 2009, definition for include.* www.Merriam-Webster.com copywright 2009, definition for aspect.*

Wallis J W et al.: "Use of volume-rendered Images in registration of nuclear medicine studies," Nuclear Science Symposium and Medical Imaging Conference, (1994) 3:3 1429-1432.

International Search Report.

William M Wells III et al., "Multi-Modal Volume Registration by Maximaization of Mutual Information", *Medical Image Analysis*, 1996, vol. 1, No. 1, pp. 35-51.

Ronald H. Huesman et al., "Deformable Registration of Multimodal Data Including Rigid Structures", *IEEE Transactions on Nuclear Science*, Jun. 2003, vol. 50, No. 3, pp. 389-392.

Paul Viola et al., "Alignment by Maximization of Mutual Information", *International Journal of Computer Vision*, vol. 24, No. 2, 1997, pp. 137-154.

A. Collignon et al., "Automated Multi-Modality Image Registration Based on Information Theory", *Information Processing in Medical Imaging*, Kluwer Academic Publishers Dordrecht, 1995, pp. 263-274.

United States Patent Application entitled "Flexible DRR Generation Using Programmable Computer Hardware", U.S. Appl. No. 10/953,342, filed Sep. 29, 2004.

* cited by examiner

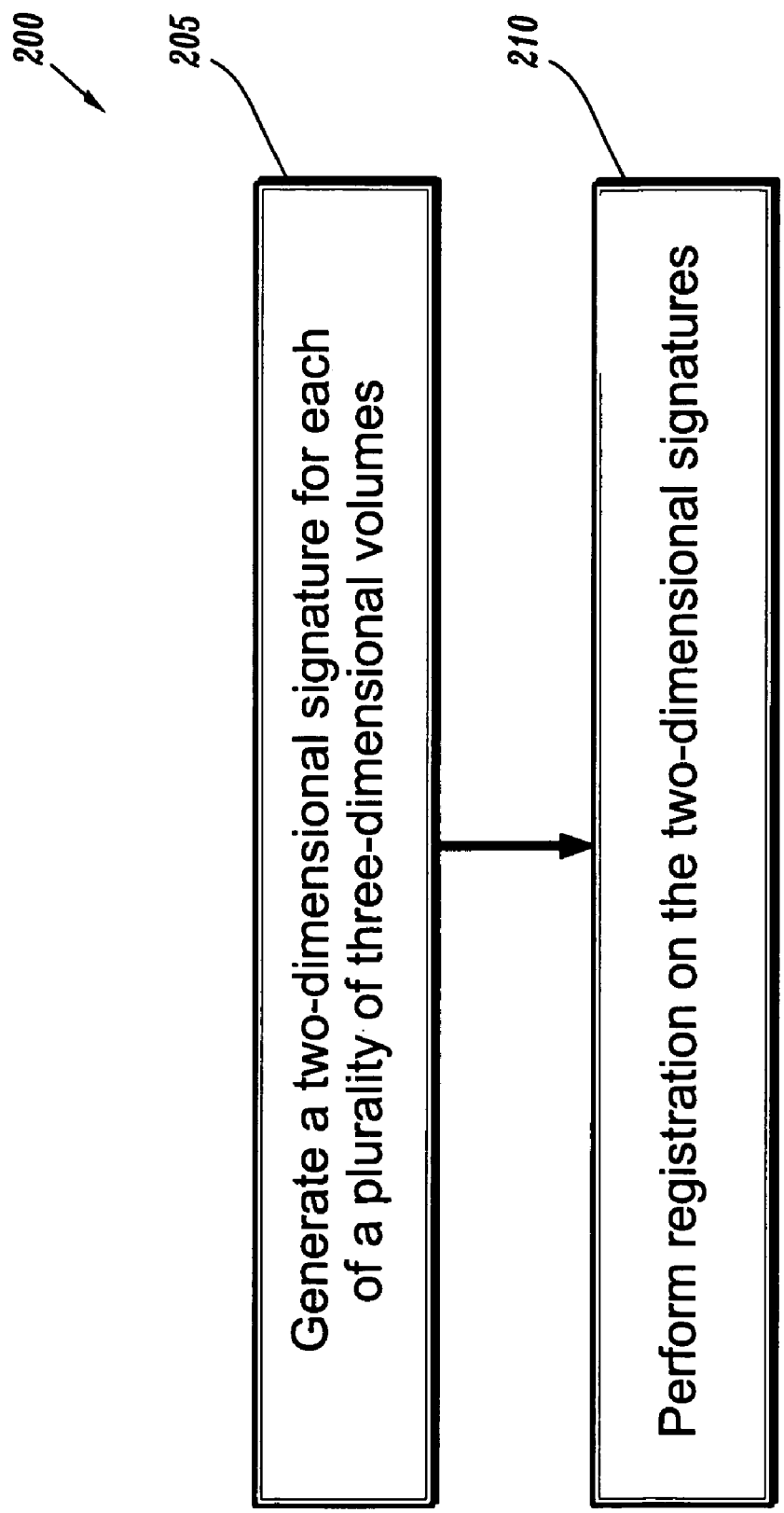

RAPID AND ROBUST 3D/3D REGISTRATION TECHNIQUE

CROSS-REFERENCE TO RELATED APPLICATIONS

This application claims priority to U.S. Provisional Application No. 60/564,145, which was filed on Apr. 21, 2004, and which is fully incorporated herein by reference.

BACKGROUND OF THE INVENTION

1. Field of the Invention

The present invention relates generally to the field of processor-based imaging, and, more particularly, to a rapid and robust 3D/3D registration method.

2. Description of the Related Art

Registration of two volumetric data sets (i.e., a fixed volume and a moving volume) generally involves three steps: (1) computing a similarity measure and/or a difference measure quantifying a metric for comparing the volumes; (2) performing an optimization scheme, which searches through the parameter space (e.g., a six-dimensional rigid body motion) to maximize the similarity measure or to minimize the difference measure; and (3) performing a volume warping method, which applies the latest computed set of parameters to the moving volume to transform the moving volume closer the fixed volume.

In multi-modal volume registration, a key issue is involves choosing a well-behaved similarity measure that can robustly characterize a metric for the volumes. Additionally, the time for computing the similarity measure and applying the similarity measure to the moving volume is of substantial importance. Current methods for computing and applying a similarity measure suggest that, for a typical three-dimensional volume data sets, the computation time is in order of minutes. Most of this time is spent on computing the similarity measure over the whole volume set, and transforming (i.e., changing the coordinate frame) of the moving volume.

Some researchers have suggested random sampling of the volume data sets and performing computations only based on these random samples to decrease the computation load. Other researchers have proposed a hybrid technique, which selects a set of high-interest points (i.e., landmarks) within the volume and attempts to perform registration based on only the set of high-interest points. In both cases, a primary goal is to reduce the computational complexity of a full-blown volumetric matching by reducing the space in which the registration is performed, while preserving the accuracy and robustness as much as possible. For many practical applications, especially for interventional scenarios, the time used for performing a registration can be quite crucial.

SUMMARY OF THE INVENTION

In one aspect of the present invention, a method is provided. The method includes the steps of generating a two-dimensional signature for each of a plurality of three-dimensional volumes; and performing registration on the two-dimensional signatures.

In another aspect of the present invention, a program storage device readable by a machine, tangibly embodying a program of instructions executable on the machine to perform method steps, is provided. The method includes the steps of generating a two-dimensional signature for each of a plurality of three-dimensional volumes; and performing registration on the two-dimensional signatures In yet another aspect of the present invention, a program storage device readable by a machine, tangibly embodying a program of instructions executable on the machine to perform method steps, is provided. The method includes the steps of generating a lower-dimension signature for each of a plurality of data sets of a given dimension; and performing registration on the lower-dimension signatures.

BRIEF DESCRIPTION OF THE DRAWINGS

The invention may be understood by reference to the following description taken in conjunction with the accompanying drawings, in which like reference numerals identify like elements, and in which:

FIG. 2 depicts a flow diagram illustrating a method in accordance with one exemplary embodiment of the present invention.

DETAILED DESCRIPTION OF PREFERRED EMBODIMENTS

Figure 1:
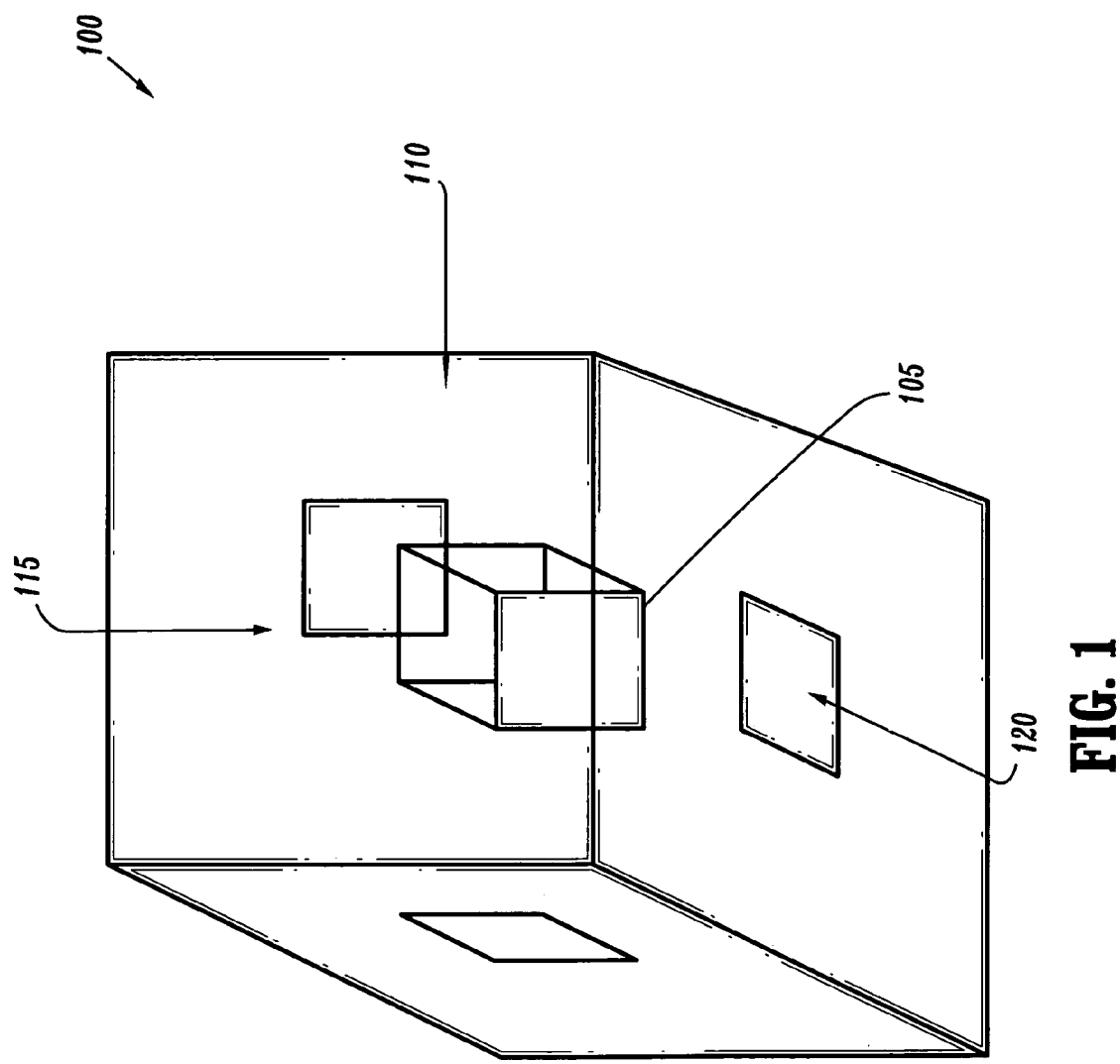
FIG. 1 depicts the generation of two-dimensional signatures from a three-dimensional volume, in accordance with one exemplary embodiment of the present invention.

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

It is to be understood that the systems and methods described herein may be implemented in various forms of hardware, software, firmware, special purpose processors, or a combination thereof. In particular, at least a portion of the present invention is preferably implemented as an application comprising program instructions that are tangibly embodied on one or more program storage devices (e.g., hard disk, magnetic floppy disk, RAM, ROM, CD ROM, etc.) and executable by any device or machine comprising suitable architecture, such as a general purpose digital computer having a processor, memory, and input/output interfaces. It is to be further understood that, because some of the constituent system components and process steps depicted in the accompanying Figures are preferably implemented in software, the connections between system modules (or the logic flow of method steps) may differ depending upon the manner in which the present invention is programmed. Given the teachings herein, one of ordinary skill in the related art will be able to contemplate these and similar implementations of the present invention.

We propose a novel method for rigidly registering two multi-modal or mono-modal volumetric data sets. A primarily bottleneck in the computational effectiveness of traditional volumetric registration algorithms is volume transformation and similarity measure estimation over the volumes. In the approach proposed herein, we downgrade the three-dimensional problem to a two-dimensional one. We consider two-dimensional signatures of the volumes (e.g., multiple maximum intensity projections ("MIPs") or digitally reconstructed radiographs ("DRRs")) as the working space where the similarity measures are computed. Therefore, we achieve much greater computational efficiency by reducing the dimension of the working space.

Multiple two-dimensional signatures can robustly represent a volume, depending on the way the signatures are generated. An easy way to conceptualize the idea is to understand the motion of an object by looking only at three perpendicular shadows of the object. By also considering see-through shadows (i.e., DRRs), we can achieve even greater robustness in our registration method. Referring now to FIG. 1, an exemplary object 105 is shown with three shadows: a first shadow projecting from the x-axis 110, a second shadow projecting from the y-axis 115, and a third shadow projecting from the z-axis 120.

We propose using multiple two dimensional signatures of three-dimensional volumes to perform registration. The number, orientation, and type of the two dimensional signature may vary depending on application. Exemplary two-dimensional signatures include, but are not limited to, planar projective (i.e., DRR), maximum intensity, and multi-planar reconstruction. The two-dimensional signature may also be non-planar (i.e., two-dimensional manifolds).

Two-dimensional signatures may have either one value or multiple values at each pixel position (x, y). Having multiple values at each pixel position encodes greater information about the represented volume than having only one value. In one exemplary embodiment of having multiple values at each pixel location, a set of two-layer projection images have minimum and maximum voxel intensities of the parallel rays intersecting the volume. Generating a two-dimensional signature may include generating a plurality of vector elements for each of a plurality of three-dimensional volumes. Each of the plurality of vector elements can store a value representing an aspect of a projection line through the corresponding three-dimensional volume.

Transformation parameters, the use of which the two-dimensional projections are transformed, is inherently smaller than that of three-dimensional volumes. For example, if the volume is transformed about an axis, the orthographic projection along the same axis remains unchanged. Furthermore, the effect of two rotational transformations about the axes in the plane perpendicular to the projection axis is minimized and the small rotations can be ignored. Therefore, the number of parameters to be changed and optimized for alignment of projection images is three. Collective registration of the projection images should cover the whole space of rigid transformation comprising six parameters (i.e., three rotations and three translations). Collective registration can be done using an iterative method during which a subset of parameters is optimized. The result here is the optimization process becomes more robust and the capture range increases solely because the number of parameters decrease.

Steering of the parallel rays in the space of the search parameters (for example, in the case of the rigid body motion, three translations and three rotations) to generate moving volume two-dimensional signatures can be implemented using graphics hardware accelerated technique as described in Guering et al., Flexible DRR Generation using Programmable Computer Hardware, Ser. No. 10/953,342 and filed on Sep. 29, 2004, and assigned to the assignee of the present application. The full disclosure of the above-referenced patent application is hereby incorporated herein by reference. Steering of the parallel rays in the space of the search parameters to generate moving volume two-dimensional signatures can be implemented using the standard rapid orthographic volume rendering technique (e.g., sheer-warp method.)

By segmenting the two-dimensional signatures, we can isolate the area of the interest with in the volume and perform selective matching on that area only. Piecewise rigid matching can be implemented by segmenting the two-dimensional signatures into multiple areas, where each area will then have its own set of parameters to perform matching/registration. Parametric non-rigid matching of the two volumetric data sets can also be performed. As the number of parameters modeling the non-rigid motion grows, a greater number of two-dimensional signatures is generally required.

Referring now to FIG. 2, an exemplary method 200 is shown, in accordance with one embodiment of the present invention. A two-dimensional signature is generated (at 205) for each of a plurality of three-dimensional volumes. A registration is performed (at 210) on the two-dimensional signatures.

The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

What is claimed is:

1. A method of registering a first volume with a second and different second volume, the method comprising:

generating by a processor three two-dimensional (2D) signatures for the first volume where each corresponds to a different one of three orthogonal directions;

generating by the processor three 2D signatures for the second volume where each corresponds to a different one of the three orthogonal directions;

registering by the processor the 2D signatures of the first volume with the 2D signatures of the second volume for each same orthogonal direction to generate three transformations; and registering by the processor the first volume with the second volume using the three generated transformations, wherein each pixel position of each 2D signature includes a minimum voxel intensity and maximum voxel intensity of a ray intersecting the corresponding 3D volume through the corresponding orthogonal direction and each 2D signature further includes rotation information and translation information of the corresponding 3D volume.

2. The method of claim 1, wherein generating a two-dimensional signature comprises: generating a planar projective of the corresponding volume at the corresponding orthogonal direction.

3. The method of claim 1, wherein generating a two-dimensional signature comprises: generating a multi-planar reconstruction of the corresponding volume at the corresponding orthogonal direction.

4. The method of claim 1, wherein generating a two dimensional signature comprises: generating a non-planar reconstruction of the corresponding volume at the corresponding orthogonal direction.

5. The method of claim 1, wherein the two-dimensional signature are generated using a graphics processing unit (GPU).

6. The method of claim 5, wherein the two-dimensional signatures are generated by steering parallel rays in a transformation space of search parameters using a GPU-accelerated technique.

7. The method of claim 5, wherein the two-dimensional signatures are generated by steering parallel rays in a transformation space of search parameters using an orthographic volume rendering technique on the GPU.

8. The method of claim 1, further comprising:
segmenting the two-dimensional signatures for isolating an area of interest; and
performing selective matching in the area of interest.

9. The method of claim 1, further comprising:
segmenting the two-dimensional signatures for isolating a plurality of areas; and
performing piecewise rigid matching on the plurality of areas.

10. The method of claim 1, further comprising:
segmenting the two-dimensional signatures for isolating a plurality of areas; and
performing non-rigid matching on the plurality of areas.

11. The method of claim 1, further comprising: simultaneously optimizing search parameters for each of the two-dimensional signatures.

12. The method of claims 11, further comprising: iteratively optimizing the search parameters for each of the two-dimensional signatures.

13. The method of claims 1, wherein registering a 2D signatures of a first volume with a 2D signatures of a second volume, comprises: calculating a similarity measure on the two-dimensional signatures.

14. A method of registering a first volume with a second and different volume, the method comprising:
generating by a processor three two-dimensional (2D) signatures for the first volume where each corresponds to a different one of three orthogonal directions;
generating by the processor three 2D signatures for the second volume where each corresponds to a different one of the three orthogonal directions;
registering by the processor the 2D signatures of the first volume with the 2D signatures of the second volume for each same orthogonal direction to generate three transformations; and
registering by the processor the first volume with the second volume using the three generated transformations,
wherein each pixel position of each 2D signature includes a minimum voxel intensity and maximum voxel intensity of a ray intersecting the corresponding 3D volume through the corresponding orthogonal direction.

15. A method of registering a first volume with a second and different volume, the method comprising:
generating by the processor three two-dimensional (2D) signatures for the first volume where each corresponds to a different one of three orthogonal directions;
generating by the processor three 2D signatures for the second volume where each corresponds to a different one of the three orthogonal directions;
registering by the processor the 2D signatures of the first volume with the 2D signatures of the second volume for each same orthogonal direction to generate three transformations; and
registering by the processor the first volume with second volume using the three generated transformations,
wherein each pixel position of each 2D signature includes a voxel intensity of a ray intersecting the corresponding 3D volume through the corresponding orthogonal direction.

\* \* \* \* \*